US012721817B1

(12) United States Patent
Kotte et al.

(10) Patent No.: US 12,721,817 B1
(45) Date of Patent: Sep. 1, 2026

(54) DELAYED-RELEASE FORMULATION OF DULOXETINE

(71) Applicant: Almatica Pharma LLC, Morristown, NJ (US)

(72) Inventors: Arundhathi Kotte, Denville, NJ (US); Raghav Gupta, Morris Plains, NJ (US); Rama Yarasani, Edison, NJ (US); Wei Luo, Montvale, NJ (US); Jitendrakumar Rathod, Parsippany, NJ (US); Erin Breloff, Norwich, NY (US); Lisle Britton, Sherburne, NY (US)

(73) Assignee: Almatica Pharma LLC, Morristown, NJ (US)

( * ) Notice: Subject to any disclaimer, the term of this patent is extended or adjusted under 35 U.S.C. 154(b) by 0 days.

(21) Appl. No.: 19/447,663

(22) Filed: Jan. 13, 2026

(51) Int. Cl.
*A61K 9/50* (2006.01)
*A61K 31/381* (2006.01)

(52) U.S. Cl.
CPC ............ *A61K 9/5078* (2013.01); *A61K 9/501* (2013.01); *A61K 9/5015* (2013.01); *A61K 9/5047* (2013.01); *A61K 31/381* (2013.01)

(58) Field of Classification Search
CPC .... A61K 9/5078; A61K 31/381; A61K 9/501; A61K 9/5047; A61K 9/5015
See application file for complete search history.

(56) References Cited

U.S. PATENT DOCUMENTS

| | | | | |
|---|---|---|---|---|
| 9,839,626 | B1 * | 12/2017 | Agarwal | A61K 9/1629 |
| 2014/0342053 | A1 * | 11/2014 | Penhasi | B01J 13/22<br>426/303 |
| 2021/0128511 | A1 * | 5/2021 | Schobel | A61K 9/006 |
| 2025/0205160 | A1 | 6/2025 | Agnihotri et al. | |

FOREIGN PATENT DOCUMENTS

| | | |
|---|---|---|
| CN | 102846566 A | 1/2013 |

OTHER PUBLICATIONS

Ganesh et al. (Asian J. of Chemistry 35(11); 2023).*
Álvarez-González, I., et al., "Genotoxic and Oxidative Effect of Duloxetine on Mouse Brain and Liver Tissues," Scientific Reports 11:6897 (Mar. 2021).
Bayne, A.-C., et al., "N-nitrosamine Mitigation with Nitrite Scavengers in Oral Pharmaceutical Drug Products," Journal of Pharmaceutical Sciences 112(7):1794-1800, Elsevier, Netherlands (Jul. 2023).
Fine, J., et al., "Nitrosamine Acceptable Intakes Should Consider Variation in Molecular Weight: The Implication of Stoichiometric DNA Damage," Regulatory Toxicology & Pharmacology, 145:105505, Elsevier, Netherlands (Dec. 2023).
Gopireddy, R.R., "Determination of Potential Nitrosamines NDMA, NDIPA and N-Nitroso Duloxetine in Duloxetine Hydrochloride by LC-MS/MS using APCI Source," Materials Today: Proceedings, 68(1):A7-A20 (2022).

* cited by examiner

*Primary Examiner* — Shirley V Gembeh
(74) *Attorney, Agent, or Firm* — Sterne, Kessler, Goldstein & Fox P.L.L.C.

(57) ABSTRACT

The present disclosure relates to pharmaceutical compositions comprising a plurality of duloxetine-containing beads, and methods of treating a depressive disorder, anxiety disorder, or pain with the compositions.

8 Claims, No Drawings

DELAYED-RELEASE FORMULATION OF DULOXETINE

FIELD

The present disclosure relates to pharmaceutical compositions comprising a plurality of duloxetine containing beads, and methods of treating a depressive disorder, anxiety disorder, or pain with the compositions.

BACKGROUND

N-nitrosamines are organic compounds having the chemical structure of a nitroso group bonded to an amine, as shown below.

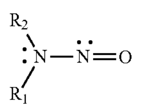

N-nitrosamines can be found in the environment and are produced endogenously. Pharmaceutical products can be contaminated with low molecular weight N-nitrosamines such as N-nitrosodimethylamine (NDMA), N-nitrosodiethylamine (NDEA), N-nitrosomethylphenylethylamine (NMPA), N-nitrosodiisopropylamine (NDIPA), N-nitrosoisophenylethylamine (NIPEA), N-nitrosodibutylamine (NDBA), and N-nitroso-N-methyl-4-aminobutyric acid (NMBA). N-nitrosamines can form in pharmaceutical products after degradation of active pharmaceutical ingredients (APIs) containing primary, secondary, tertiary or quaternary amine groups in their structures. This degradation can occur when nitrites, which are present in some excipients, including but not limited to, lactose, pregelatinized starch, magnesium stearate, stearic acid, and silicon dioxide are converted into nitrous anhydride, which is a nitrosating agent.

Because N-nitrosamines are classified as mutagenic and carcinogenic and have been found in certain classes of pharmaceutical products, there is a need to formulate APIs containing amine groups in their structures, including duloxetine, to mitigate the risks associated with N-nitrosamine contaminants in the drug products.

BRIEF SUMMARY

The present disclosure provides pharmaceutical compositions comprising a plurality of beads, wherein each bead in the plurality of beads comprises: a sugar sphere; a nitrosamine scavenger layer coated over the sugar sphere, the scavenger layer comprising L-cysteine or a pharmaceutically acceptable salt thereof, and hydroxypropyl methylcellulose; a drug-containing layer coated over the nitrosamine scavenger layer, the drug-containing layer comprising duloxetine hydrochloride, and hydroxypropyl methylcellulose; a seal coating layer coated over the drug-containing layer, the seal coating layer comprising L-cysteine or a pharmaceutically acceptable salt thereof, and hydroxypropyl methylcellulose, sucrose, and talc; and an enteric coating layer coated over the seal coating layer, the enteric coating layer comprising hydroxypropyl methylcellulose phthalate.

In some aspects, the enteric coating layer further comprises triethyl citrate, talc, or a combination thereof.

In some aspects, the nitrosamine scavenger is present in an amount from about 1% to about 10% by weight of the pharmaceutical composition. In some aspects, the nitrosamine scavenger is present in an amount from about 4% to about 6% by weight of the pharmaceutical composition.

In some aspects, the duloxetine, or an equivalent amount of the pharmaceutically acceptable salt thereof, is present in an amount from about 20% to about 45% by weight of the pharmaceutical composition. In some aspects, the duloxetine, or an equivalent amount of the pharmaceutically acceptable salt thereof, is present in an amount from about 15% to about 35% by weight of the pharmaceutical composition.

In some aspects, the composition comprises no more than about 1 ppm of nitrosoduloxetine after storage for 6 months at 40° C. and 75% relative humidity. In some aspects, the composition comprises no more than about 0.3 ppm of nitrosoduloxetine after storage for 6 months at 40° C. and 75% relative humidity.

In some aspects, the pharmaceutical composition is a capsule, a tablet, a mini-tablet, or a sprinkle.

The present disclosure also provides pharmaceutical compositions comprising a plurality of beads, wherein each bead in the plurality of beads comprises: an inert core; a nitrosamine scavenger layer coated over the inert core, the scavenger layer comprising a film forming agent and a nitrosamine scavenger selected from the group consisting of cysteine, histidine, glycine, arginine, ascorbic acid, α-tocopherol, pharmaceutically acceptable salts thereof, and combinations thereof; a drug-containing layer coated over the nitrosamine scavenger layer, the drug-containing layer comprising duloxetine, or a pharmaceutically acceptable salt thereof, and a film forming agent; and a seal coating layer comprising a film forming agent coated over the drug-containing layer, wherein the film forming agent is selected from the group consisting of hydroxypropyl methylcellulose, ethyl cellulose, methylcellulose, hydroxyethyl cellulose, hydroxypropyl cellulose, sodium carboxymethyl cellulose, cellulose acetate, polyvinylpyrrolidone, polyvinyl alcohol, and combinations thereof.

In some aspects, the seal coating layer further comprises a nitrosamine scavenger selected from the group consisting of cysteine, histidine, glycine, arginine, ascorbic acid, α-tocopherol, pharmaceutically acceptable salts thereof, and combinations thereof.

In some aspects, the seal coating layer further comprises a seal coating additive. In some aspects, the seal coating additive comprises sucrose, talc, or a combination thereof.

In some aspects, the drug-containing layer further comprises a nitrosamine scavenger selected from the group consisting of cysteine, histidine, glycine, arginine, ascorbic acid, α-tocopherol, pharmaceutically acceptable salts thereof, and combinations thereof.

In some aspects, each bead in the plurality of beads further comprises an enteric coating layer coated over the seal coating layer, wherein the enteric coating layer comprises an enteric polymer selected from the group consisting of methacrylic acid copolymer, cellulose acetate phthalate, cellulose acetate succinate, polymethacrylic acid/acrylic acid copolymer, hydroxypropyl methylcellulose phthalate, hydroxypropyl methylcellulose acetate succinate, polyvinyl acetate phthalate, hydroxyethyl ethyl cellulose phthalate, cellulose acetate tetrahydrophthalate, acrylic resin, and combinations thereof.

In some aspects, the enteric coating layer further comprises a plasticizer, an anti-static agent, or a combination thereof.

In some aspects, the nitrosamine scavenger is cysteine or a pharmaceutically acceptable salt thereof. In some aspects, the nitrosamine scavenger is L-cysteine.

In some aspects, the pharmaceutical composition comprises no more than about 1 ppm of nitrosoduloxetine after storage for 6 months at 40° C. and 75% relative humidity. In some aspects, the pharmaceutical composition comprises no more than about 0.9 ppm of nitrosoduloxetine after storage for 6 months at 40° C. and 75% relative humidity. In some aspects, the pharmaceutical composition comprises no more than about 0.3 ppm of nitrosoduloxetine after storage for 6 months at 40° C. and 75% relative humidity.

In some aspects, the nitrosamine scavenger is present in an amount from about 1% to about 10% by weight of the pharmaceutical composition. In some aspects, the nitrosamine scavenger is present in an amount from about 3% to about 8% by weight of the pharmaceutical composition. In some aspects, the nitrosamine scavenger is present in an amount from about 4% to about 6% by weight of the pharmaceutical composition.

In some aspects, the duloxetine, or an equivalent amount of the pharmaceutically acceptable salt thereof, is present in an amount from about 20% to about 45% by weight of the pharmaceutical composition. In some aspects, the duloxetine, or an equivalent amount of the pharmaceutically acceptable salt thereof, is present in an amount from about 25% to about 40% by weight of the pharmaceutical composition. In some aspects, the duloxetine, or an equivalent amount of the pharmaceutically acceptable salt thereof, is present in an amount from about 25% to about 35% by weight of the pharmaceutical composition.

In some aspects, the inert core comprises a sugar sphere, a microcrystalline cellulose sphere, or an isomalt sphere.

In some aspects, the pharmaceutical composition is a capsule, a tablet, a mini-tablet, or a sprinkle.

The present disclosure also provides a capsule dosage form comprising a plurality of beads, wherein each bead in the plurality of beads comprises: a sugar sphere; a nitrosamine scavenger layer coated over the sugar sphere, the scavenger layer comprising L-cysteine or a pharmaceutically acceptable salt thereof, and hydroxypropyl methylcellulose; a drug-containing layer coated over the nitrosamine scavenger layer, the drug-containing layer comprising duloxetine hydrochloride, and hydroxypropyl methylcellulose; a seal coating layer coated over the drug-containing layer, the seal coating layer comprising L-cysteine or a pharmaceutically acceptable salt thereof, and hydroxypropyl methylcellulose, sucrose, and talc; and an enteric coating layer coated over the seal coating layer, the enteric coating layer comprising hydroxypropyl methylcellulose phthalate.

In some aspects, the enteric coating layer further comprises triethyl citrate, talc, or a combination thereof.

In some aspects, the nitrosamine scavenger is present in an amount from about 1% to about 7% by weight of the capsule dosage form. In some aspects, the nitrosamine scavenger is present in an amount from about 3% to about 6% by weight of the capsule dosage form. In some aspects, the nitrosamine scavenger is present in an amount from about 4% to about 5% by weight of the capsule dosage form.

In some aspects, the duloxetine, or an equivalent amount of the pharmaceutically acceptable salt thereof, is present in an amount from about 15% to about 35% by weight of the capsule dosage form. In some aspects, the duloxetine, or an equivalent amount of the pharmaceutically acceptable salt thereof, is present in an amount from about 20% to about 30% by weight of the capsule dosage form. In some aspects, the duloxetine, or an equivalent amount of the pharmaceutically acceptable salt thereof, is present in an amount from about 25% to about 30% by weight of the capsule dosage form.

The present disclosure also provides coated beads comprising: an inert core; a nitrosamine scavenger layer coated over the inert core, the scavenger layer comprising a film forming agent and a nitrosamine scavenger selected from the group consisting of cysteine, histidine, glycine, arginine, ascorbic acid, α-tocopherol, pharmaceutically acceptable salts thereof, and combinations thereof; a drug-containing layer coated over the nitrosamine scavenger layer, the drug-containing layer comprising duloxetine, or a pharmaceutically acceptable salt thereof, and a film forming agent; and a seal coating layer comprising a film forming agent coated over the drug-containing layer, wherein the film forming agent is selected from the group consisting of hydroxypropyl methylcellulose, ethyl cellulose, methylcellulose, hydroxyethyl cellulose, hydroxypropyl cellulose, sodium carboxymethyl cellulose, cellulose acetate, polyvinylpyrrolidone, polyvinyl alcohol, and combinations thereof.

In some aspects, the seal coating layer further comprises a nitrosamine scavenger selected from the group consisting of cysteine, histidine, glycine, arginine, ascorbic acid, α-tocopherol, pharmaceutically acceptable salts thereof, and combinations thereof.

In some aspects, the coated beads further comprise an enteric coating layer coated over the seal coating layer, wherein the enteric coating layer comprises an enteric polymer selected from the group consisting of methacrylic acid copolymer, cellulose acetate phthalate, cellulose acetate succinate, polymethacrylic acid/acrylic acid copolymer, hydroxypropyl methylcellulose phthalate, hydroxypropyl methylcellulose acetate succinate, polyvinyl acetate phthalate, hydroxyethyl ethyl cellulose phthalate, cellulose acetate tetrahydrophthalate, acrylic resin, and combinations thereof.

In some aspects, the nitrosamine scavenger is cysteine or a pharmaceutically acceptable salt thereof. In some aspects, the nitrosamine scavenger is L-cysteine.

In some aspects, the nitrosamine scavenger is present in an amount from about 1% to about 10% by weight of the coated beads. In some aspects, the nitrosamine scavenger is present in an amount from about 3% to about 8% by weight of the coated beads. In some aspects, the nitrosamine scavenger is present in an amount from about 4% to about 6% by weight of the coated beads.

In some aspects, the duloxetine, or an equivalent amount of the pharmaceutically acceptable salt thereof, is present in an amount from about 20% to about 45% by weight of the coated beads. In some aspects, the duloxetine, or an equivalent amount of the pharmaceutically acceptable salt thereof, is present in an amount from about 25% to about 40% by weight of the coated beads. In some aspects, the duloxetine, or an equivalent amount of the pharmaceutically acceptable salt thereof, is present in an amount from about 25% to about 35% by weight of the coated beads.

In some aspects, the inert core comprises a sugar sphere, a microcrystalline cellulose sphere, or an isomalt sphere.

The present disclosure also provides methods of treating a depressive disorder, an anxiety disorder, or pain, comprising administering to a subject in need thereof the pharmaceutical composition, the capsule dosage form, or the coated beads as described herein above. In some aspects, the depressive disorder is a major depressive disorder. In some aspects, the pain is a neuropathic pain, fibromyalgia, or a musculoskeletal pain. In some aspects, the pain is diabetic peripheral neuropathic pain, fibromyalgia, or chronic musculoskeletal pain.

The present disclosure also provides methods of preparing the duloxetine-containing bead as described herein above, comprising the steps of: a) coating an inert core with a nitrosamine scavenger composition, wherein the nitrosamine scavenger composition comprises a film forming agent and a nitrosamine scavenger selected from the group consisting of cysteine, histidine, glycine, arginine, ascorbic acid, α-tocopherol, pharmaceutically acceptable salts thereof, and combinations thereof, to obtain a bead coated with a nitrosamine scavenger layer; b) drying the bead coated with the nitrosamine scavenger layer to form a dried bead; c) coating the dried bead with a drug-containing composition to form a drug-coated bead, wherein the drug-containing composition comprises duloxetine, or a pharmaceutically acceptable salt thereof, and a film forming agent, to obtain a bead coated with a drug-containing layer; d) drying the bead coated with a drug-containing layer to form a dried drug-coated bead; e) coating the dried drug-coated bead with a seal coating composition to form a seal-coated bead, wherein the seal coating composition comprises a film forming agent, to obtain a bead coated with a seal coating layer; and f) drying the seal-coated bead to form the duloxetine-containing bead, wherein the film forming agent is selected from the group consisting of hydroxypropyl methylcellulose, ethyl cellulose, methylcellulose, hydroxyethyl cellulose, hydroxypropyl cellulose, sodium carboxymethyl cellulose, cellulose acetate, polyvinylpyrrolidone, polyvinyl alcohol, and combinations thereof.

In some aspects, the seal coating composition further comprises a nitrosamine scavenger selected from the group consisting of cysteine, histidine, glycine, arginine, ascorbic acid, α-tocopherol, pharmaceutically acceptable salts thereof, and combinations thereof.

In some aspects, the method further comprises: g) coating the seal-coated bead with an enteric coating composition, wherein the enteric coating composition comprises an enteric polymer selected from the group consisting of methacrylic acid copolymer, cellulose acetate phthalate, cellulose acetate succinate, polymethacrylic acid/acrylic acid copolymer, hydroxypropyl methylcellulose phthalate, hydroxypropyl methylcellulose acetate succinate, polyvinyl acetate phthalate, hydroxyethyl ethyl cellulose phthalate, cellulose acetate tetrahydrophthalate, acrylic resin, and combinations thereof.

DETAILED DESCRIPTION

Duloxetine is a selective serotonin and norepinephrine reuptake inhibitor (SSNRI), which is used for the treatment of major depressive disorder (MDD) in adults, generalized anxiety disorder (GAD) in adults and pediatric populations of 7 years and older, diabetic peripheral neuropathic pain in adults, fibromyalgia in adults and pediatric patients 13 years of age and older, and chronic musculoskeletal pain in adults.

Duloxetine contains a secondary amine group in its structure, as shown below:

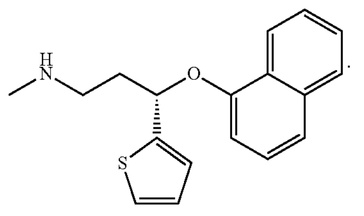 [SMILES: CNCC[C@H](Oc1cccc2ccccc12)c1cccs1]

The secondary amine group of duloxetine can potentially react with excipient derived nitrites and form N-nitroso duloxetine B (NDXT), as shown below:

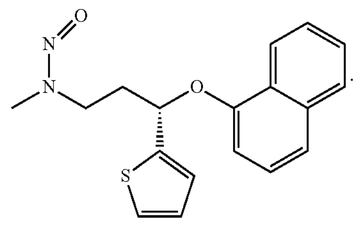 [SMILES: CN(CC[C@H](Oc1cccc2ccccc12)c1cccs1)N=O]

According to the U.S. Food & Drug Administration (FDA) and the European Medicines Agency (EMA), the acceptable intake of NDXT is 100 ng/day.

It has now been surprisingly found that the present formulation, inclusive of the beads and of dosage forms comprising such beads as described herein, not only achieves nitrosamine levels within or below the acceptable limits, but also maintains nitrosamine levels within or below the acceptable limits under accelerated and long-term stability conditions.

Definitions

The singular forms “a,” “an,” and “the” include plural referents unless the context clearly dictates otherwise.

As used herein, the term “or” is a logical disjunction (i.e., and/or) and does not indicate an exclusive disjunction unless expressly indicated as such with the terms “either,” “unless,” “alternatively,” and words of similar effect.

As used herein, the term “about” refers to +5% of the noted value, unless otherwise specified, and unless the upper bound of the range would exceed 100% of the composition, in which case the upper limit of the range is limited to 99.9%. Thus, and by way of example only, a composition including about 10 weight percent of a given ingredient could have from 9.5 to 10.5 weight percent of the compound. Similarly, a composition including about 95 weight percent of a given ingredient could have from 90.25 to 99.75 weight percent of the ingredient in the composition.

As used herein, the term “coated” refers to a layer, or a film that is directly or indirectly applied, either completely or partially, over the surface of a substrate, or over another layer.

As used herein, the term “inert core” refers to any inert material or mixture of materials known in the art of drug formulation that does not interact adversely with a drug substance. Exemplary inert cores include, but are not limited to, a sugar (sucrose) sphere, a pellet of microcrystalline cellulose, an isomalt sphere, a mannitol sphere, a lactose sphere, or a starch sphere. Other suitable inert cores are known to those of skill in the art. The inert core can have a particle size ranging from about 300 μm to about 1700 μm, such as from about 500 μm to about 600 μm.

As used herein, the term “nitrosamine scavenger” refers to a substance that inhibits, or reduces the formation of NDXT in a duloxetine-containing drug product. Exemplary nitrosamine scavengers include, but are not limited to, cysteine, histidine, glycine, lysine, arginine, meglumine, ascorbic acid, α-tocopherol, caffeic acid, ferulic acid, butylated hydroxyanisole (BHA), butylated hydroxytoluene (BHT), para-aminobenzoic acid (PABA), maltol, propyl gallate, pharmaceutically acceptable salts thereof, and combinations thereof.

As used herein, the term "duloxetine" refers to duloxetine or a pharmaceutically acceptable salt thereof, including a hydrate or a solvate thereof, and crystalline and amorphous forms thereof.

As used herein, the term "film forming agent" refers to a polymeric material that creates a thin layer or film over a surface. Exemplary film forming agents include, but are not limited to, cellulose derivatives, polyvinylalcohol (PVA), polyvinylpyrrolidone (PVP), and polyacrylic acid. Exemplary cellulose derivatives include, but are not limited to, hydroxypropyl methylcellulose, ethyl cellulose, methylcellulose, hydroxyethyl cellulose, hydroxypropyl cellulose, sodium carboxymethyl cellulose, cellulose acetate, polyvinylpyrrolidone, polyvinyl alcohol, and combinations thereof.

Duloxetine-Coated Beads

Certain aspects of the disclosure are directed to a coated bead comprising: an inert core; a nitrosamine scavenger layer coated over the inert core, the scavenger layer comprising a film forming agent and a nitrosamine scavenger selected from the group consisting of cysteine, histidine, glycine, arginine, ascorbic acid, α-tocopherol, pharmaceutically acceptable salts thereof, and combinations thereof; a drug-containing layer coated over the nitrosamine scavenger layer, the drug-containing layer comprising duloxetine, or a pharmaceutically acceptable salt thereof, and a film forming agent; and a seal coating layer comprising a film forming agent coated over the drug-containing layer, wherein the film forming agent is selected from the group consisting of hydroxypropyl methylcellulose, ethyl cellulose, methylcellulose, hydroxyethyl cellulose, hydroxypropyl cellulose, sodium carboxymethyl cellulose, cellulose acetate, polyvinylpyrrolidone, polyvinyl alcohol, and combinations thereof.

As used herein, the term "bead," "particle," or "pellet" are used interchangeably.

In some aspects, the inert core comprises a sugar sphere, or a pellet of microcrystalline cellulose. In some aspects, the inert core comprises a sugar sphere. In some aspects, the inert core is present in an amount of not more than about 50% by weight of the bead. In some aspects, the nitrosamine scavenger layer coated core is present in a weight ratio of about 1:1 to about 1.5:1 relative to the drug-containing layer.

In some aspects, the nitrosamine scavenger is cysteine, histidine, glycine, lysine, arginine, α-tocopherol, pharmaceutically acceptable salts thereof, or a combination thereof. In some aspects, the nitrosamine scavenger is L-cysteine, α-tocopherol, pharmaceutically acceptable salts thereof, or a combination thereof. In some aspects, the nitrosamine scavenger is L-cysteine, or a pharmaceutically acceptable salt thereof, such as L-cysteine hydrochloride. In some aspects, the nitrosamine scavenger is L-cysteine.

In some aspects, the drug-containing layer contains duloxetine hydrochloride. In some aspects, duloxetine, or an equivalent amount of duloxetine hydrochloride, is about 20% to about 45%, about 20% to about 40%, about 25% to about 40%, about 25% to about 35%, or about 25% to about 30% by weight of the coated bead. In some aspects, the drug-containing layer is present in an amount of about 30% to about 45% by weight of the coated bead.

In some aspects, the film forming agent is hydroxypropyl methylcellulose, ethyl cellulose, methylcellulose, hydroxyethyl cellulose, hydroxypropyl cellulose, or a combination thereof. In some aspects, the film forming agent is hydroxypropyl methylcellulose (hypromellose or HPMC), and is about 3% to about 8%, about 4% to about 8%, about 5% to about 8%, or about 5% to 7% by weight of the coated bead.

In certain aspects, the seal coating layer further comprises a nitrosamine scavenger. In some aspects, the nitrosamine scavenger is selected from the group consisting of cysteine, histidine, glycine, arginine, ascorbic acid, α-tocopherol, pharmaceutically acceptable salts thereof, and combinations thereof. In some aspects, the nitrosamine scavenger is L-cysteine, α-tocopherol, pharmaceutically acceptable salts thereof, or a combination thereof. In some aspects, the nitrosamine scavenger is L-cysteine, or a pharmaceutically acceptable salt thereof, such as L-cysteine hydrochloride. In some aspects, the nitrosamine scavenger is L-cysteine.

In some aspects, the total amount of nitrosamine scavenger in each bead is about 0.5% to about 10%, about 1% to about 10%, about 2% to about 9%, about 3% to about 8%, about 4% to about 7%, or about 4% to about 6% by weight of the coated bead.

In some aspects, the nitrosamine scavenger in the nitrosamine scavenger layer and the seal coating layer is L-cysteine, and is about 3% to about 9%, about 4% to about 8%, about 4% to about 7%, or about 4% to 6%, about 3%, about 3.5%, about 4%, about 4.5%, about 5%, about 5.5%, about 6%, about 6.5%, about 7%, about 7.5%, or about 8% by weight of the coated bead. In some aspects, the amount of L-cysteine in the seal coating layer is about 20% to about 35%, about 20% to about 30%, or about 25% to about 30% by weight of total L-cysteine, with the remaining amount being present in the nitrosamine scavenger layer.

In some aspects, the seal coating layer further comprises a seal coating additive that does not interact adversely with duloxetine. Suitable additives include, but are not limited to a plasticizer, a barrier coating adjunct, an anti-static agent, and combinations thereof. Exemplary plasticizers include but are not limited to propylene glycol, triethyl citrate, tributyl citrate, dibutyl sebacate, acetyl tributyl citrate, glyceryl monostearate, triacetin, diethyl phthalate, acetylated monoglycerides, diacetylated monoglycerides, cetyl alcohol, and mixtures thereof. Exemplary barrier coating adjuncts include but are not limited to, sugars such as mannitol, lactose, fructose, and sucrose. Exemplary antistatic agents include but are not limited to talc, glycerol monostearate, magnesium stearate, silica, and mixtures thereof. In some aspects, the seal coating layer can further comprise sucrose, talc, and combinations thereof. In some aspects, the seal coating layer is present in an amount of about 5% to about 15% by weight of the coated bead.

In some aspects, the drug-containing layer further comprises a nitrosamine scavenger selected from the group consisting of cysteine, histidine, glycine, arginine, ascorbic acid, α-tocopherol, pharmaceutically acceptable salts thereof, and combinations thereof. In some aspects, the nitrosamine scavenger is L-cysteine, α-tocopherol, pharmaceutically acceptable salts thereof, or a combination thereof. In some aspects, the nitrosamine scavenger is L-cysteine.

In certain aspects, the bead further comprises an enteric coating layer coated over the seal coating layer. The enteric coating layer comprises an enteric polymer that dissolves at a pH of above about 5.5. Exemplary enteric polymers include but are not limited to methacrylic acid copolymer, cellulose acetate phthalate, cellulose acetate succinate, polymethacrylic acid/acrylic acid copolymer, hydroxypropyl methylcellulose phthalate, hydroxypropyl methylcellulose acetate succinate, polyvinyl acetate phthalate, hydroxyethyl ethyl cellulose phthalate, cellulose acetate tetrahydrophthalate, acrylic resin, and combinations thereof. In some aspects, the enteric polymer is methacrylic acid copolymer, polymethacrylic acid/acrylic acid copolymer, hydroxypropyl methylcellulose phthalate, or a combination thereof. In some aspects, the enteric polymer is hydroxypropyl methylcellulose phthalate. In some aspects, the enteric polymer is about 55% to about 95%, about 65% to about 85%, or about 70% to about 80% by weight of the enteric coating layer.

In some aspects, the enteric coating layer further comprises one or more additional pharmaceutically acceptable excipients that do not interact adversely with duloxetine. Suitable excipients include but are not limited to a plasticizer, an anti-static agent, and combinations thereof. Suitable plasticizers include but are not limited to propylene glycol, triethyl citrate, tributyl citrate, dibutyl sebacate, acetyl tributyl citrate, glyceryl monostearate, triacetin, diethyl phthalate, acetylated monoglycerides, diacetylated monoglycerides, cetyl alcohol, and mixtures thereof. In some aspects, the plasticizer is triethyl citrate. Suitable anti-static agents include but are not limited to talc, glycerol monostearate, magnesium stearate, silica, and mixtures thereof. In some aspects, the anti-static agent is talc. In some aspects, the enteric coating layer further comprises triethyl citrate, talc, or a combination thereof.

In certain aspects, the bead described herein has an initial N-nitroso duloxetine B (NDXT) level (i.e. at t=0) below about 1.00 ppm, below about 0.90 ppm, below about 0.80 ppm, below about 0.70 ppm, below about 0.60 ppm, below about 0.50 ppm, below about 0.40 ppm, below about 0.30 ppm, or below about 0.25 ppm. In some aspects, the bead described herein maintains an NDXT level below about 1.00 ppm, below about 0.90 ppm, below about 0.80 ppm, below about 0.70 ppm, below about 0.60 ppm, below about 0.50 ppm, below about 0.40 ppm, or below about 0.30 ppm after 3 or 6 months at 40° C. and 75% relative humidity. In some aspects, the bead described herein maintains an NDXT level below about 1.00 ppm, below about 0.90 ppm, below about 0.80 ppm, below about 0.70 ppm, below about 0.60 ppm, below about 0.50 ppm, below about 0.40 ppm, below about 0.30 ppm, or below 0.25 ppm after 3 or 6 months at 25° C. and 60% relative humidity.

In some aspects, the bead described herein maintains an NDXT level of no more than about 0.30 ppm, no more than about 0.40 ppm, no more than about 0.50 ppm, no more than about 0.60 ppm, no more than about 0.70 ppm, no more than about 0.80 ppm, or no more than about 0.90 ppm after 3 or 6 months at 40° C. and 75% relative humidity. In some aspects, the bead described herein maintains an NDXT level of no more than about 0.25 ppm, no more than about 0.30 ppm, no more than about 0.40 ppm, no more than about 0.50 ppm, no more than about 0.60 ppm, no more than about 0.70 ppm, no more than about 0.80 ppm, or no more than about 0.90 ppm after 3 or 6 months at 25° C. and 60% relative humidity.

Pharmaceutical Compositions

Certain aspects of the disclosure are directed to a pharmaceutical composition comprising a plurality of the duloxetine coated beads described herein.

In some aspects, the pharmaceutical composition is in the form of a capsule, a tablet, a mini-tablet, or a sprinkle.

In some aspects, the composition further comprises one or more pharmaceutically acceptable excipients, including diluents, binders, disintegrants, lubricants, glidants, or combinations thereof.

Suitable diluents include, but are not limited to, lactose, microcrystalline cellulose, starch, pregelatinized starch, mannitol, sorbitol, xylitol, lactitol, and mixtures thereof.

Suitable binders include but are not limited to cellulose derivatives, such as methylcellulose, hydroxypropyl cellulose, hydroxypropyl methylcellulose ethylcellulose, hydroxyl ethyl cellulose, L-hydroxy propyl cellulose; polyvinylpyrrolidone, such as povidone, copovidone; starch, such as cornstarch, pre-gelatinized starch and hydroxypropyl starch; and mixtures of any of the foregoing.

Suitable disintegrants include but are not limited to low substituted hydroxypropyl cellulose, crospovidone, crosscarmellose sodium, and mixtures thereof.

Suitable lubricants include but are not limited to magnesium stearate, calcium stearate, zinc stearate, stearic acid, hydrogenated vegetable oil, hydrogenated castor oil, glyceryl palmitostearate, sodium stearyl fumarate, mineral oil, talc, and mixtures thereof.

Suitable glidants include but are not limited to talc, colloidal silicon dioxide, magnesium trisilicate, tribasic calcium phosphate and mixtures thereof.

In some aspects, the nitrosamine scavenger is present in an amount from about 1% to about 10%, about 3% to about 8%, or about 4% to about 6% by weight of the pharmaceutical composition.

In some aspects, the duloxetine, or an equivalent amount of a pharmaceutically acceptable salt thereof, is present in an amount from about 20% to about 45%, about 25% to about 40%, about 25% to about 30%, or about 15% to about 35% by weight of the pharmaceutical composition.

Duloxetine Delayed Release Capsules

Certain aspects of the disclosure are directed to a capsule dosage form comprising a plurality of beads, wherein each bead in the plurality of beads comprises: a sugar sphere; a nitrosamine scavenger layer coated over the sugar sphere, the scavenger layer comprising L-cysteine or a pharmaceutically acceptable salt thereof, and hydroxypropyl methylcellulose; a drug-containing layer coated over the nitrosamine scavenger layer, the drug-containing layer comprising duloxetine hydrochloride, and hydroxypropyl methylcellulose; a seal coating layer coated over the drug-containing layer, the seal coating layer comprising L-cysteine or a pharmaceutically acceptable salt thereof, and hydroxypropyl methylcellulose, sucrose, and talc; and an enteric coating layer coated over the seal coating layer, the enteric coating layer comprising hydroxypropyl methylcellulose phthalate.

In some aspects, the enteric coating layer further comprises one or more additional pharmaceutically acceptable excipients that do not interact adversely with duloxetine. Suitable excipients include but are not limited to a plasticizer, an anti-static agent, or a combination thereof. In some aspects, the enteric coating layer further comprises triethyl citrate, talc, or a combination thereof. In some aspects, the enteric coating layer further comprises about 0.5% to about 3% by weight of triethyl citrate and about 0.5% to about 6% by weight of talc.

In some aspects, the nitrosamine scavenger is present in an amount from about 1% to about 7%, about 3% to about 6%, or about 4% to about 5% by weight of the capsule dosage form.

In some aspects, the duloxetine, or an equivalent amount of a pharmaceutically acceptable salt thereof, is present in an amount from about 15% to about 35%, about 20% to about 30%, or about 25% to about 30% by weight of the capsule dosage form.

In some aspects, the capsule dosage form comprises a plurality of beads, wherein each bead in the plurality of beads comprises: about 20% to about 45% by weight of sugar sphere (based on the total weight of the bead); a L-cysteine layer coated over the sugar sphere, which comprises about 2% to about 9% by weight of L-cysteine, and 0.05% to about 5% by weight of hydroxypropyl methylcellulose; a duloxetine-containing layer coated over the L-cysteine layer, which comprises about 25% to about 35% by weight of duloxetine (in an equivalent amount duloxetine hydrochloride), and about 1% to about 8% by weight of hydroxypropyl methylcellulose; a seal coating layer coated over the drug-containing layer, which comprises about 0.5% to about 2% by weight of L-cysteine, and about 0.5% to about 3% by weight of hydroxypropyl methylcellulose, about 1% to about 10% by weight of sucrose, and about 0.5% to about 5% by weight of talc; and an enteric coating layer coated over the seal coating layer, which comprises 5% to about 15% by weight of hydroxypropyl methylcellulose phthalate.

The capsule dosage form as described herein may contain additional pharmaceutical excipients as an extragranular component, such as a glidant. Exemplary glidants include but are not limited to talc, colloidal silicon dioxide, magnesium trisilicate, powdered cellulose, starch, tribasic calcium phosphate; and mixtures thereof. In some aspects, the capsule dosage form comprise talc, and colloidal silicon dioxide as the extragranular component.

Methods of Treatment

Certain aspects of the disclosure are directed to a method treating a depressive disorder, an anxiety disorder, or pain, comprising administering to a subject in need thereof an effective amount of the coated beads, the pharmaceutical composition, or the capsule dosage form as described herein above. In some aspects, the depressive disorder to be treated is a major depressive disorder. In some aspects, the pain to be treated is a neuropathic pain, fibromyalgia, or a musculoskeletal pain. In some aspects, the pain to be treated is diabetic peripheral neuropathic pain, fibromyalgia, or chronic musculoskeletal pain. In some aspects, the subject is a human patient.

Method of Preparing Duloxetine-Containing Beads

Certain aspects of the disclosure are directed to a method of preparing a duloxetine-containing bead, comprising the steps of:

a) coating an inert core with a nitrosamine scavenger composition, wherein the nitrosamine scavenger composition comprises a film forming agent and a nitrosamine scavenger selected from the group consisting of cysteine, histidine, glycine, arginine, ascorbic acid, α-tocopherol, pharmaceutically acceptable salts thereof, and combinations thereof, to obtain a bead coated with a nitrosamine scavenger layer;

b) drying the bead coated with the nitrosamine scavenger layer to form a dried bead;

c) coating the dried bead with a drug-containing composition to form a drug-coated bead, wherein the drug-containing composition comprises duloxetine, or a pharmaceutically acceptable salt thereof, and a film forming agent, to obtain a bead coated with a drug-containing layer;

d) drying the bead coated with a drug-containing layer to form a dried drug-coated bead;

e) coating the dried drug-coated bead with a seal coating composition to form a seal-coated bead, wherein the seal coating composition comprises a film forming agent, to obtain a bead coated with a seal coating layer; and f) drying the seal-coated bead to form the duloxetine-containing bead, wherein the film forming agent is selected from the group consisting of hydroxypropyl methylcellulose, ethyl cellulose, methylcellulose, hydroxyethyl cellulose, hydroxypropyl cellulose, sodium carboxymethyl cellulose, cellulose acetate, polyvinylpyrrolidone, polyvinyl alcohol, and combinations thereof.

In some aspects, the seal coating composition further comprises a nitrosamine scavenger selected from the group consisting of cysteine, histidine, glycine, arginine, ascorbic acid, α-tocopherol, pharmaceutically acceptable salts thereof, and combinations thereof. In some aspects, the nitrosamine scavenger is L-cysteine.

In some aspects, the method further comprises: g) coating the seal-coated bead with an enteric coating composition, wherein the enteric coating composition comprises an enteric polymer selected from the group consisting of methacrylic acid copolymer, cellulose acetate phthalate, cellulose acetate succinate, polymethacrylic acid/acrylic acid copolymer, hydroxypropyl methylcellulose phthalate, hydroxypropyl methylcellulose acetate succinate, polyvinyl acetate phthalate, hydroxyethyl ethyl cellulose phthalate, cellulose acetate tetrahydrophthalate, acrylic resin, and combinations thereof.

Each step of the process may be performed by any method known in the art of pharmaceutical formulation. For example, the nitrosamine scavenger composition may be applied to the inert core by any suitable conventional techniques, such as pan coating, fluid bed coating, or spray drying.

In some aspects, a nitrosamine scavenger (e.g., L-cysteine) composition is a solution, and is prepared in a suitable solvent (e.g., purified water). The solution is applied to inert cores (e.g., sugar spheres) by fluid bed coating to obtain beads coated with the nitrosamine scavenger layer.

In some aspects, a duloxetine-containing composition is a suspension, and is prepared in a suitable solvent (e.g., purified water). The suspension is applied to the beads coated with a nitrosamine scavenger layer by fluid bed coating to obtain beads coated with a duloxetine-containing layer.

In some aspects, a seal coating composition is a suspension, and is prepared in a suitable solvent (e.g., purified water). The suspension is applied to the beads coated with a duloxetine-containing layer by fluid bed coating to obtain beads coated with a seal coating layer.

In some aspects, an enteric coating composition is a suspension, and is prepared in a suitable solvent (e.g., mixture of alcohol and purified water). The suspension is applied to the beads coated with a seal coating layer by fluid bed coating to obtain beads coated with an entering coating layer.

EXAMPLES

The following examples are offered by way of illustration and not by way of limitation.

Example 1

Duloxetine Delayed Release Capsules without Nitrosamine Scavenger

TABLE 1

| Ingredients | Sample 1 % Composition |
|---|---|
| Sugar spheres, NF | 32.5 |
| Duloxetine hydrochloride, USP | 33 |
| Hypromellose, USP | 3.7 |
| Purified water, USP, EP[1] | Qs |
| Seal coating | |
| Hypromellose, USP | 1.4 |
| Sucrose, NF | 4.1 |
| Talc, USP | 4.9 |
| Purified water, USP, EP[1] | Qs |
| Enteric coating | |
| Hypromellose phthalate, NF | 14 |
| Triethyl citrate, NF | 1.7 |
| Talc, USP | 4.2 |
| Dehydrated alcohol (200 Proof), USP[2] | Qs |
| Purified water, USP, EP[1] | Qs |
| Blending | |
| Talc, USP | 0.2 |
| Colloidal silicon dioxide, NF, EP | 0.2 |
| Total | 100 |
| Nitrosamines (acceptable limit: 0.83 ppm) | 1.6 ppm |

[1]Water is evaporated during processing.
[2]Dehydrated alcohol (200 Proof) is evaporated during processing.

Hypromellose was added slowly into purified water and stirred to obtain a clear solution. To the hypromellose solution, duloxetine hydrochloride was added slowly and stirred to obtain a homogeneous suspension.

The fluid bed was pre-heated, and the sugar spheres were loaded into the fluid bed until the sugar spheres reached 28° C. to 48° C. The resulting heated spheres were fluidized under gentle fluidization. After achieving optimum fluidization, the drug coating suspension was sprayed. After completion of spraying, the beads were dried for 10 to 90 minutes at 29° C. to 49° C. The dried drug coated beads were screened to remove the overs and fines.

Hypromellose was added slowly to purified water and stirred to obtain a clear solution. To the hypromellose solution, sucrose was added slowly and stirred to obtain a clear solution. To the sucrose solution, talc was added slowly and stirred, until the solids are completely dispersed. The suspension was then homogenized.

The fluid bed was pre-heated and the drug coated beads were loaded until the drug coated beads reached 30° C. to 50° C. The resulting heated beads were fluidized under gentle fluidization. After achieving optimum fluidization, the seal coating suspension was sprayed. After completion of spraying, the seal coated beads were dried for 10 to 90 minutes at 32° C. to 52° C. and screened to remove the overs and fines.

Hypromellose phthalate was added slowly into ethanol-purified water and stirred to obtain a clear solution.

Ethanol-purified water was added to the container. To this, triethyl citrate was added slowly and stirred until completely dissolved. Talc was added slowly to the solution and stirred until the solids were completely dispersed and the suspension was then homogenized. The talc/triethyl citrate suspension was added to the hypromellose phthalate solution and the stirring continued.

The fluid bed was pre-heated and the seal coated beads were loaded until the seal coated beads reached 20° C. to 40° C. The resulting heated beads were fluidized under gentle fluidization. After achieving optimum fluidization, the enteric coating suspension was sprayed. After completion of spraying, the enteric coated beads were dried at 35° C.-60° C. for 10 to 90 minutes and screened to remove the overs and fines. After screening, the beads were cured for 12 to 36 hours.

The enteric coated beads, colloidal silicon dioxide, and talc were loaded into the bin blender and blended for 5 to 20 minutes.

The blended beads were encapsulated.

The blended beads were evaluated for nitrosamines using liquid chromatography-mass spectroscopy (LC-MS) analytical method and the results are listed in Table 1. The results demonstrated that the nitrosamine level (1.6 ppm) in the duloxetine delayed release capsules, which do not contain a nitrosamine scavenger, exceeded the acceptable limit (0.83 ppm).

Example 2

Duloxetine Coated Beads with and without Nitrosamine Scavengers

TABLE 2

| Ingredients | Sample 2a % Composition | Sample 2b % Composition | Sample 2c % Composition |
|---|---|---|---|
| Sugar spheres, NF | 47 | 44.5 | 43.4 |
| Duloxetine hydrochloride, USP | 47.7 | 47.7 | 47.7 |
| Hypromellose, USP | 5.3 | 5.3 | 5.3 |
| Sodium lauryl sulfate, NF | N/A | 1.4 | N/A |
| Vitamin E (α-tocopherol), USP | N/A | 1.1 | N/A |
| Sodium ascorbate, USP | N/A | N/A | 3.5 |
| Purified water, USP, EP[1] | Qs | Qs | Qs |
| Drug coated beads | 100 | 100 | 100 |
| Nitrosamines (acceptable limit: 0.83 ppm) | 2.1 ppm | 0.79 ppm | 1.21 ppm |

[1]Water is evaporated during processing.

Hypromellose was added slowly into purified water and stirred to obtain a clear solution. To the hypromellose solution, duloxetine hydrochloride was added slowly and stirred to obtain a homogeneous suspension.

To make the duloxetine coated beads of Sample 2a, the fluid bed was pre-heated and the sugar spheres were loaded into the fluid bed. After achieving optimum fluidization, the drug suspension was sprayed. After completion of spraying, the beads were dried. The dried drug coated beads were screened to remove the overs and fines.

To make the duloxetine coated beads of Sample 2b, sodium lauryl sulfate was added slowly into purified water and stirred to obtain a clear solution. To the sodium lauryl sulfate solution, Vitamin E was added slowly and stirred to obtain a homogeneous solution. To the Vitamin E solution, hypromellose was added slowly and stirred to obtain a homogeneous solution. To the solution, duloxetine hydrochloride was added slowly and stirred to obtain a homogeneous suspension. The fluid bed was pre-heated and the sugar spheres were loaded into the fluid bed. After achieving optimum fluidization, the drug coating suspension was sprayed. After completion of spraying, the beads were dried. The dried drug coated beads were screened to remove the overs and fines.

To make the duloxetine coated beads of Sample 2c, sodium ascorbate was added slowly into purified water and stirred to obtain a clear solution. To the sodium ascorbate solution, hypromellose was added slowly and stirred to obtain a homogeneous solution. To the solution, duloxetine hydrochloride was added slowly and stirred to obtain a homogeneous suspension.

The fluid bed was pre-heated and the sugar spheres were loaded into the fluid bed until the sugar spheres reached 21° C. to 48° C. The resulting heated spheres were fluidized under gentle fluidization. After achieving optimum fluidization, the drug coating suspension was sprayed. After completion of spraying, the beads were dried at 25° C.-55° C. for 10 to 90 minutes. The dried drug coated beads were screened to remove the overs and fines.

The beads were evaluated for nitrosamines and the results are listed in Table 2. The inclusion of nitrosamine scavengers lowered nitrosamine levels in Samples 2b and 2c. However, the nitrosamine level of Sample 2c still exceeded the acceptable limit, whereas the nitrosamine level of Sample 2b met the acceptable limit. The nitrosamine formation is attributed to the presence of excipient-derived nitrites, particularly from the sugar spheres that comprise about 47% (Sample 2a), about 44.5% (Sample 2b), and about 43.4% (Sample 2c) by weight based on the total weight of the bead compositions.

Example 3

Duloxetine Coated Beads Containing Nitrosamine Scavengers in a Seal Coating

TABLE 3

| Ingredients | Sample 3a % Composition | Sample 3b % Composition | Sample 3c % Composition | Sample 3d % Composition |
|---|---|---|---|---|
| Seal coated sugar spheres containing nitrosamine scavengers | Vitamin E | Sodium ascorbate | L-cysteine hydrochloride monohydrate | L-cysteine |
| Sugar spheres, NF | 44.1 | 41.8 | 41.2 | 41.8 |
| Hydroxy propyl cellulose, NF | 1.6 | N/A | N/A | N/A |
| Hypromellose, USP | N/A | 1.6 | 1.6 | 1.6 |
| Vitamin E (α-tocopherol), USP | 1.1 | N/A | N/A | N/A |
| Sodium ascorbate, USP | N/A | 3.5 | N/A | N/A |
| L-cysteine hydrochloride monohydrate | N/A | N/A | 5 | N/A |
| L-cysteine | N/A | N/A | N/A | 3.5 |
| Talc, USP | 0.5 | N/A | N/A | N/A |
| Purified water, USP, EP[1] | N/A | Qs | Qs | Qs |
| Dehydrated alcohol (200 Proof), USP[2] | Qs | N/A | N/A | N/A |
| Drug-containing layer | | | | |
| Duloxetine hydrochloride, USP | 47.5 | 47.7 | 47 | 47.8 |
| Hypromellose, USP | 5.3 | 5.3 | 5.2 | 5.3 |
| Purified water, USP, EP[2] | Qs | Qs | Qs | Qs |
| Drug coated beads | 100 | 100 | 100 | 100 |
| Nitrosamines in drug coated beads (acceptable limit: 0.83 ppm) | 0.6 ppm | 2.8 ppm | 0.6 ppm | 0.5 ppm |

[1]Water is evaporated during processing.

[2]Dehydrated alcohol (200 Proof) is evaporated during processing.

Vitamin E was added slowly into the dehydrated alcohol (200 Proof) and stirred to obtain a clear solution. To the Vitamin E solution, hydroxy propyl cellulose was added slowly and stirred to obtain a clear solution. To the solution, talc was added slowly and stirred to obtain a homogeneous suspension.

Sodium ascorbate was added slowly into purified water and stirred to obtain a clear solution. To the sodium ascorbate solution, hypromellose was added slowly and stirred to obtain a clear solution.

L-cysteine hydrochloride monohydrate was added slowly into purified water and stirred to obtain a clear solution. To the L-cysteine hydrochloride monohydrate solution, hypromellose was added slowly and stirred to obtain a clear solution.

L-cysteine was added slowly into purified water and stirred to obtain a clear solution. To the L-cysteine solution, hypromellose was added slowly and stirred to obtain a clear solution.

The fluid bed was pre-heated and each of the Vitamin E sugar spheres, sodium ascorbate sugar spheres, or L-cysteine hydrochloride monohydrate sugar spheres were loaded into the fluid bed until the sugar spheres reached 18° C.-50° C. The resulting heated spheres were fluidized under gentle fluidization. After achieving optimum fluidization, each of the Vitamin E, sodium ascorbate or L-cysteine hydrochloride monohydrate solution was sprayed. After completion of spraying, the beads were dried at 30° C.-50° C. for 10 to 90 minutes. The dried coated beads were screened to remove the overs and fines.

Hypromellose was added slowly into purified water and stirred to obtain a clear solution. To the hypromellose solution, duloxetine hydrochloride was added slowly and stirred to obtain a homogeneous suspension.

The fluid bed was pre-heated, and each of the Vitamin E coated beads, sodium ascorbate coated beads, or L-cysteine hydrochloride monohydrate coated beads was loaded into the fluid bed until the coated beads reached 18° C.-45° C. The resulting heated beads were fluidized under gentle fluidization. After achieving optimum fluidization, the drug suspension was sprayed. After completion of spraying, the beads were dried at 30° C.-50° C. for 10 to 90 minutes. The dried drug coated beads were screened to remove the overs and fines.

The drug containing beads were evaluated for nitrosamines and the results are listed in Table 3. The results demonstrated that the nitrosamine levels of Samples 3a and 3c met the acceptable limit and the nitrosamine level of Sample 3b exceeded the acceptable limits. The results also demonstrated that the inclusion of nitrosamine scavengers in the seal coating that covers the sugar spheres, instead of in the drug layer (Example 2), lowered the nitrosamine levels, when comparing Sample 3a against Sample 2b. Because duloxetine hydrochloride is known to be acid-labile, and L-cysteine hydrochloride monohydrate is acidic, the drug-coated beads (Sample 3c) containing L-cysteine hydrochloride monohydrate as the scavenger were analyzed for impurities along with the control containing no scavenger (Sample 1). The results are summarized in Table 4.

TABLE 4

| Related compounds | Specification | Sample 1 T0 | Sample 3c T0 |
|---|---|---|---|
| Related Compound - B (Duloxetine Alcohol) | NMT 0.2% LC | <0.05 | 0.21 |
| Related Compound - D (α-Naphthol) | NMT 0.2% LC | <0.05 | 0.33 |
| Related Compound - C (Duloxetine-4-naphthyl isomer) | NMT 0.2% LC | <0.05 | <0.05 |
| Related Compound - E (Duloxetine β-naphthol-1-yl-isomer) | NMT 0.2% LC | <0.05 | 0.09 |
| Related Compound - H | NMT 0.2% LC | <0.05 | ND |
| Related Compound - F | NMT 0.2% LC | — | <0.05 |
| Any individual unspecified degradation product | NMT 0.2% LC | 0.10 | 0.12 |
| Total degradation products | NMT 0.4% LC | 0.10 | 0.75 |

T0 means initial time.
NMT means no more than.
ND means not detected.

Based on the results from Table 4, higher impurity contents were detected in Sample 3c as compared to Sample 1.

Example 4

Duloxetine Coated Beads Containing L-Cysteine in a Seal Coating

TABLE 5

| Ingredients | Sample 4 % Composition |
|---|---|
| Seal coated sugar spheres containing L-cysteine | |
| Sugar spheres, NF | 36.4 |
| Hypromellose, USP | 1.4 |
| L-cysteine | 3.1 |
| Purified water, USP, EP[1] | Qs |
| Drug-containing layer | |
| Duloxetine hydrochloride, USP | 41.5 |
| Hypromellose, USP | 4.6 |
| Purified water, USP, EP[1] | Qs |
| Nitrosamines in drug coated beads (limit: 0.83 ppm) | 0.5 |
| Seal coating | |
| Hypromellose, USP | 1.7 |
| Sucrose, NF | 5.1 |
| Talc, USP | 6.2 |
| Purified water, USP, EP[1] | Qs |
| Seal coated beads | 100 |
| Nitrosamines in seal coated drug beads (acceptable limit: 0.83 ppm) | 1.1 ppm |

[1]Water is evaporated during processing.

L-cysteine was added slowly into purified water and stirred to obtain a clear solution. To the L-cysteine solution, hypromellose was added slowly and stirred to obtain a clear solution.

The fluid bed was pre-heated, and the sugar spheres were loaded into the fluid bed until the sugar spheres reached 25° C.-45° C. The resulting heated spheres were fluidized under gentle fluidization. After achieving optimum fluidization, the L-cysteine solution was sprayed. After completion of spraying, the beads were dried at 31° C.-51° C. for 10 to 90 minutes. The dried coated beads were screened to remove the overs and fines.

Hypromellose was added slowly into purified water and stirred to obtain a clear solution. To the hypromellose solution, duloxetine hydrochloride was added slowly and stirred to obtain a homogeneous suspension.

The fluid bed was pre-heated, and the L-cysteine coated beads were loaded into the fluid bed until the L-cysteine coated beads reached 18° C.-40° C. The resulting heated beads were fluidized under gentle fluidization. After achieving optimum fluidization, the drug suspension was sprayed. After completion of spraying, the drug coated beads were dried at 29° C.-49° C. for 10 to 90 minutes. The dried drug coated beads were screened to remove the overs and fines.

Hypromellose was added slowly to purified water and stirred to obtain a clear solution. To the hypromellose solution, sucrose was added slowly and stirred to obtain a clear solution. To the sucrose solution, talc was added slowly and stirred, until the solids were completely dispersed. The suspension was then homogenized for 10 to 30 minutes.

The fluid bed was pre-heated, and the drug coated beads were loaded until the drug coated beads reached 25° C.-45° C. The resulting heated beads were fluidized under gentle fluidization. After achieving optimum fluidization, the seal coating suspension was sprayed. After completion of spraying, the seal coated beads were dried at 30° C.-50° C. for 10 to 90 minutes and screened to remove the overs and fines.

The beads were evaluated for nitrosamines and the results are listed in Table 5. The results demonstrated that the inclusion of nitrosamine scavengers in the seal coating that covers the sugar spheres, resulted in drug coated beads with the acceptable nitrosamine level (0.50 ppm). However, the subsequent seal coating of the drug-layered beads increased nitrosamine levels.

Example 5

Duloxetine Coated Beads Containing L-Cysteine in Seal Coatings

TABLE 6

| Ingredients | Sample 5 % Composition |
|---|---|
| Seal coated sugar spheres containing L-cysteine | |
| Sugar spheres, NF | 43.1 |
| Hypromellose, USP | 1.3 |
| L-cysteine | 4.2 |
| Purified water, USP, EP[1] | Qs |
| Drug-containing layer | |
| Duloxetine hydrochloride, USP | 37.4 |
| Hypromellose, USP | 4.2 |
| Purified water, USP, EP[1] | Qs |
| Drug coated beads | |
| Nitrosamines in drug coated beads (limit: 0.83 ppm) | 0.35 ppm |
| Seal coating | |
| Hypromellose, USP | 1.6 |
| Sucrose, NF | 4.6 |
| L-cysteine | 1.4 |
| Talc, USP | 2.3 |
| Purified water, USP, EP[1] | Qs |
| Seal coated beads | |
| Nitrosamines in seal coated drug beads (acceptable limit: 0.83 ppm) | 0.41 ppm |

[1]Water is evaporated during processing.

L-cysteine was added slowly into purified water and stirred to obtain a clear solution. To the L-cysteine solution, hypromellose was added slowly and stirred to obtain a clear solution.

The fluid bed was pre-heated and the sugar spheres were loaded into the fluid bed until the sugar spheres reached 20° C.-42° C. The resulting heated spheres were fluidized under gentle fluidization. After achieving optimum fluidization, the L-cysteine solution was sprayed. After completion of spraying, the beads were dried at 30° C.-50° C. for 10 to 90 minutes. The dried coated beads were screened to remove the overs and fines.

Hypromellose was added slowly into purified water and stirred to obtain a clear solution. To the hypromellose solution, duloxetine hydrochloride was added slowly and stirred to obtain a homogeneous suspension. The suspension was then homogenized.

The fluid bed was pre-heated, and the L-cysteine layered beads were loaded into the fluid bed until the L-cysteine layered beads reached 20° C.-42° C. The heated beads were fluidized under gentle fluidization. After achieving optimum fluidization, the drug suspension was sprayed. After completion of spraying, the drug coated beads were dried at 32° C.-52° C. for 10 to 90 minutes. The dried drug coated beads were screened to remove the overs and fines.

L-cysteine was added slowly to purified water and stirred to obtain a clear solution. To the L-cysteine solution, hypromellose was added slowly and stirred to obtain a clear solution. To the hypromellose solution, sucrose was added slowly and stirred to obtain a clear solution. To the sucrose solution, talc was added slowly and stirred, until the solids were completely dispersed. The suspension was then homogenized for 10 to 30 minutes.

The fluid bed was pre-heated and the drug coated beads were loaded into the fluid bed until the drug coated beads reached 20° C.-42° C. The resulting heated beads were fluidized under gentle fluidization. After achieving optimum fluidization, the seal coating suspension was sprayed. After completion of spraying, the seal coated beads were dried at 30° C.-50° C. for 10 to 90 minutes and screened to remove the overs and fines.

The beads were evaluated for nitrosamines and the results are listed in Table 6. The results demonstrated that the nitrosamine level is below the acceptable limit and that the inclusion of a nitrosamine scavenger in the seal coating that covers the drug-layered beads further lowered the nitrosamine level.

Example 6

Duloxetine Delayed Release Capsules Containing L-Cysteine

TABLE 7

| Ingredients | Sample 6a % Composition | Sample 6b % Composition | Sample 6c % Composition |
|---|---|---|---|
| Seal coated sugar spheres containing L-cysteine | | | |
| Sugar spheres, NF | 38.5 | 39.7 | 39.4 |
| Hypromellose, USP | 1 | 1 | 1 |
| L-cysteine | 3.3 | 3.4 | 3.4 |
| Purified water, USP, EP[1] | Qs | Qs | Qs |
| Drug-containing layer | | | |
| Duloxetine hydrochloride, USP | 29.6 | 30.5 | 30.5 |
| Hypromellose, USP | 3.3 | 3.4 | 3.4 |
| Purified water, USP, EP[1] | Qs | Qs | Qs |

TABLE 7-continued

| Ingredients | Sample 6a % Composition | Sample 6b % Composition | Sample 6c % Composition |
|---|---|---|---|
| Seal coating on drug coated beads | | | |
| Hypromellose, USP | 1.2 | 1.3 | 1.3 |
| Sucrose, NF | 3.7 | 3.8 | 3.8 |
| L-cysteine | 1.1 | 1.1 | 1.4 |
| Talc, USP | 1.8 | 1.9 | 1.9 |
| Purified water, USP, EP[1] | Qs | Qs | Qs |
| Enteric coating | | | |
| Hypromellose phthalate, NF | 11.3 | 9.4 | 9.4 |
| Triethyl citrate, PG/NF | 1.4 | 1.1 | 1.1 |
| Talc, USP | 2.9 | 2.4 | 2.4 |
| Dehydrated alcohol (200 Proof), USP[2] | Qs | Qs | Qs |
| Purified water, USP, EP[1] | Qs | Qs | Qs |
| Blending | | | |
| Talc, USP (Pharma 700) | 0.5 | 0.5 | 0.5 |
| Colloidal silicon dioxide, NF, EP | 0.5 | 0.5 | 0.5 |
| Total | 100 | 100 | 100 |
| Nitrosamines (acceptable limit: 0.83 ppm) | 0.24 ppm | 0.32 ppm | <0.21 ppm |

[1]Water is evaporated during processing.
[2]Dehydrated alcohol (200 Proof) is evaporated during processing.

L-cysteine was added slowly into purified water and stirred to obtain a clear solution. To the L-cysteine solution, hypromellose was added slowly and stirred to obtain a clear solution.

The fluid bed was pre-heated and the sugar spheres were loaded into the fluid bed until the sugar spheres reached 30° C.-50° C. The resulting heated spheres were fluidized under gentle fluidization. After achieving optimum fluidization, the L-cysteine solution was sprayed. After completion of spraying, the beads were dried at 33° C.-56° C. for 10 to 90 minutes. The dried coated beads were screened to remove the overs and fines.

Hypromellose was added slowly into purified water and stirred to obtain a clear solution. To the hypromellose solution, duloxetine hydrochloride was added slowly and stirred to obtain a homogeneous suspension.

The fluid bed was pre-heated, and the L-cysteine coated beads were loaded into the fluid bed until the L-cysteine coated beads reached 28° C.-50° C. The resulting heated beads were fluidized under gentle fluidization. After achieving optimum fluidization, the drug suspension was sprayed. After completion of spraying, the drug coated beads were dried at 30° C.-55° C. for 10 to 90 minutes. The dried drug coated beads were screened to remove the overs and fines.

L-Cysteine was added slowly to purified water and stirred to obtain a clear solution. To the L-cysteine solution, hypromellose was added slowly and stirred to obtain a clear solution. To the hypromellose solution, sucrose was added slowly and stirred to obtain a clear solution. To the sucrose solution, talc was added slowly and stirred, until the solids were completely dispersed. The suspension was then homogenized.

The fluid bed was pre-heated, and the drug coated beads were loaded until the drug coated beads reached 30° C.-52° C. The resulting heated beads were fluidized under gentle fluidization. After achieving optimum fluidization, the seal coating suspension was sprayed. After completion of spraying, the seal coated beads were dried at 30° C.-52° C. for 10 to 90 minutes and screened to remove the overs and fines.

Hypromellose phthalate was added slowly into ethanol-purified water and stirred to obtain a clear solution. Triethyl citrate was added slowly to the ethanol-purified water and stirred until completely dissolved. Talc was added slowly to the solution and stirred until the solids were completely dispersed. The solution was then homogenized. The talc/triethyl citrate suspension was added to the hypromellose phthalate solution and the stirring continued.

The fluid bed was pre-heated, and the seal coated beads were loaded until the seal coated beads reached 18° C.-–38° C. The resulting heated beads were fluidized under gentle fluidization. After achieving optimum fluidization, the enteric coating suspension was sprayed. After completion of spraying, the enteric coated beads were dried at 35° C.-60° C. for 40 to 90 minutes and screened to remove the overs and fines. After screening, the beads were cured for 12 to 36 hours.

Enteric coated beads, colloidal silicon dioxide and talc were loaded into the bin blender and blended for 5 to 20 minutes.

The blended beads were encapsulated.

The blended beads were evaluated for nitrosamines and the results are listed in Table 7. The results demonstrated that nitrosamine levels were significantly below the acceptable limit.

The nitrosamine levels of the capsules of Sample 6c were monitored under accelerated and long-term stability conditions. The resulting stability data is summarized in Table 8.

TABLE 8

| Stability Condition | 40° C./75% RH | | | 25° C./60% RH | |
|---|---|---|---|---|---|
| | T0 | 3 Months | 6 Months | 3 Months | 6 Months |
| Nitrosamines (ppm) (limit: 0.83 ppm) | <0.21 | 0.27 | 0.28 | 0.22 | 0.21 |

Based on the results in Table 8, the nitrosamine levels were significantly below the acceptable limits under both conditions. In addition, no significant difference was observed in nitrosamine levels from T0 to 6 months.

Example 7

Comparison of Certain Formulations

TABLE 9

| Ingredients | Sample 7a (Comparative) % Composition | Sample 7b (Inventive) % Composition |
|---|---|---|
| L-cysteine layering on sugar spheres | | |
| Sugar spheres, NF | NA | 45.8 |
| L-cysteine | NA | 3.9 |
| Hypromellose, USP | NA | 1.2 |
| Purified water, USP, EP[1] | NA | Qs |
| Drug-containing layer | | |
| Sugar spheres, NF | 46.4 | NA |
| Duloxetine hydrochloride, USP | 35.9 | 35.5 |
| Hypromellose, USP | 4.0 | 3.95 |
| L-cysteine | 5.6 | NA |
| Purified water, USP, EP[1] | Qs | Qs |

TABLE 9-continued

| Ingredients | Sample 7a (Comparative) % Composition | Sample 7b (Inventive) % Composition |
|---|---|---|
| Seal coating on drug coated beads | | |
| L-cysteine | NA | 1.6 |
| Hypromellose, USP | 1.5 | 1.5 |
| Sucrose, NF | 4.4 | 4.4 |
| Talc, USP | 2.2 | 2.2 |
| Purified water, USP, EP[1] | Qs | Qs |
| Total | 100 | 100 |
| Nitrosamines (acceptable limit: 0.83 ppm) | 0.35 ppm | 0.27 ppm |

[1]Water is evaporated during processing.

A comparative study was conducted to assess the similarity of formulations as described herein against formulations described in U.S. Patent Pub. No. 2025/0205160. For purposes of this study, the enteric coating layer was omitted as it was not expected to contribute to the lowering of the nitrosamine levels.

Sample 7b was prepared according to the procedure used to prepare Sample 6c except that Sample 7b did not contain the enteric coating layer for the reasons noted above. As a result of this omission, the percentages reported in Table 9 for Sample 7b are different than the percentages in Table 7 for Sample 6c, however the actual amounts of each element used in Sample 7b were identical to the amounts used in Sample 6c.

Sample 7a was prepared according to the procedures reported in 2025/0205160. In order to make sure that the comparison between Samples 7a and 7b was appropriate, the total amount of L-cysteine used in each formulation was identical as was the total amount of duloxetine HCl.

The drug coated and seal coated beads were evaluated for nitrosamines. The results surprisingly demonstrated that Sample 7a, which included the nitrosamine scavenger solely in the drug-containing layer, did not yield duloxetine beads capable of reducing nitrosamine impurity formation to a sufficient extent suitable for use in a dosage form. Indeed, Sample 7a led to 30% higher nitrosamines than Sample 7b, as demonstrated in Table 9. Thus, it was surprisingly found that, although Sample 7a and Sample 7b contained the same total amount of the nitrosamine scavenger, the inventive formulation provided substantially and surprisingly better nitrosamine control.

It is to be appreciated that the Detailed Description, and not the Summary and Abstract sections, is intended to be used to interpret the claims. The Summary and Abstract sections may set forth one or more, but not all exemplary embodiments as contemplated by the inventor(s), and thus, are not intended to limit the appended claims in any way.

The embodiments provided herein have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the various embodiments described herein that others can, by applying knowledge within the skill of the art, readily modify and/or adapt for various applications such specific embodiments, without undue experimentation, without departing from the general concept of the present disclosure. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary embodiments, but should be defined only in accordance with the following claims and their equivalents.

What is claimed is:

1. A pharmaceutical composition comprising a plurality of beads, wherein each bead in the plurality of beads comprises:

a sugar sphere;

a nitrosamine scavenger layer coated over the sugar sphere, the scavenger layer comprising L-cysteine or a pharmaceutically acceptable salt thereof, and hydroxypropyl methylcellulose;

a drug-containing layer coated over the nitrosamine scavenger layer, the drug-containing layer comprising duloxetine hydrochloride, and hydroxypropyl methylcellulose;

a seal coating layer coated over the drug-containing layer, the seal coating layer comprising L-cysteine or a pharmaceutically acceptable salt thereof, and hydroxypropyl methylcellulose, sucrose, and talc; and an enteric coating layer coated over the seal coating layer, the enteric coating layer comprising hydroxypropyl methylcellulose phthalate;

wherein the L-cysteine or the pharmaceutically acceptable salt thereof is present in a total amount from about 1% to about 10% by weight of the pharmaceutical composition;

wherein the seal coating layer comprises about 20% to about 35% by weight of the total amount of the L-cysteine or the pharmaceutically acceptable salt thereof, with the remaining L-cysteine or pharmaceutically acceptable salt thereof being present in the nitrosamine scavenger layer; and wherein the L-cysteine inhibits the formation of nitrosoduloxetine.

2. The pharmaceutical composition according to claim 1, wherein the enteric coating layer further comprises triethyl citrate, talc, or a combination thereof.

3. The pharmaceutical composition according to claim 1, wherein the duloxetine, or an equivalent amount of the pharmaceutically acceptable salt thereof, is present in an amount from about 20% to about 45% by weight of the pharmaceutical composition.

4. The pharmaceutical composition according to claim 3, wherein the duloxetine, or an equivalent amount of the pharmaceutically acceptable salt thereof, is present in an amount from about 15% to about 35% by weight of the pharmaceutical composition.

5. The pharmaceutical composition according to claim 1, wherein the composition comprises no more than about 1 ppm of nitrosoduloxetine after storage for 6 months at 40° C. and 75% relative humidity.

6. The pharmaceutical composition according to claim 5, wherein the composition comprises no more than about 0.3 ppm of nitrosoduloxetine after storage for 6 months at 40° C. and 75% relative humidity.

7. The pharmaceutical composition according to claim 1, wherein the pharmaceutical composition is a capsule, a tablet, a mini-tablet, or a sprinkle.

8. The pharmaceutical composition according to claim 1, wherein the total amount of L-cysteine is from about 4% to about 6% by weight of the pharmaceutical composition.

* * * * *